(12) United States Patent
Simhambhatla

(10) Patent No.: US 6,620,128 B1
(45) Date of Patent: Sep. 16, 2003

(54) BALLOON BLOWING PROCESS WITH METERED VOLUMETRIC INFLATION

(75) Inventor: Murthy V. Simhambhatla, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 119 days.

(21) Appl. No.: 09/693,063

(22) Filed: Oct. 20, 2000

(51) Int. Cl.$^7$ ............................................. A61M 29/00
(52) U.S. Cl. .................................................. 604/97.01
(58) Field of Search .............................. 604/96, 97.01, 604/103; 264/454, 464, 496, 563

(56) References Cited

U.S. PATENT DOCUMENTS

| | | | |
|---|---|---|---|
| 4,490,421 A | * 12/1984 | Levy | 428/35 |
| 4,906,244 A | 3/1990 | Pinchuk et al. | 606/194 |
| 5,087,394 A | 2/1992 | Keith | |
| 5,156,612 A | 10/1992 | Pinchuk et al. | |
| 5,223,205 A | 6/1993 | Jackowski et al. | 264/521 |
| 5,304,340 A | 4/1994 | Downey | |
| 5,306,246 A | 4/1994 | Sahatjian et al. | 604/96 |
| 5,330,428 A | 7/1994 | Wang et al. | 604/96 |
| 5,449,371 A | 9/1995 | Pinchuk et al. | 606/194 |
| 5,556,383 A | 9/1996 | Wang et al. | |
| 5,738,653 A | 4/1998 | Pinchuk et al. | 604/96 |
| 5,830,182 A | 11/1998 | Wang et al. | 604/96 |
| 6,004,289 A | * 12/1999 | Saab | 604/96 |
| 6,398,780 B1 | * 6/2002 | Farley et al. | 604/104 |

FOREIGN PATENT DOCUMENTS

WO    WO 00/51660    9/2000

* cited by examiner

Primary Examiner—Edward K. Look
Assistant Examiner—Kimya N McCoy
(74) Attorney, Agent, or Firm—Fulwider Patton Lee & Utecht, LLP

(57) ABSTRACT

A balloon for a balloon catheter and a method of manufacture The method entails providing a polymeric tubular member having an inner lumen and a longitudinal axis. An incompressible fluid is introduced into the inner lumen at a predetermined volumetric flow rate, expanding the polymeric tubular member to a desired outer diameter. The volumetric flow rate of fluid may be predetermined to not over-inflate the balloon. The balloon is blown slower because no initial pressure need be exceeded, so higher blow up ratios may be achieved without sacrificing any strength of the balloon. The balloons embodying features of the invention have thinner walls, yet maintain the same physical and mechanical properties of a thicker walled balloon manufactured in today's methods. Therefore, the process of the invention will lead to lower profile balloon catheters for balloon catheters with the same outer diameter balloon on them. Alternatively, a balloon with the same wall thickness as a balloon made from standard techniques will yield a much stronger balloon.

19 Claims, 2 Drawing Sheets

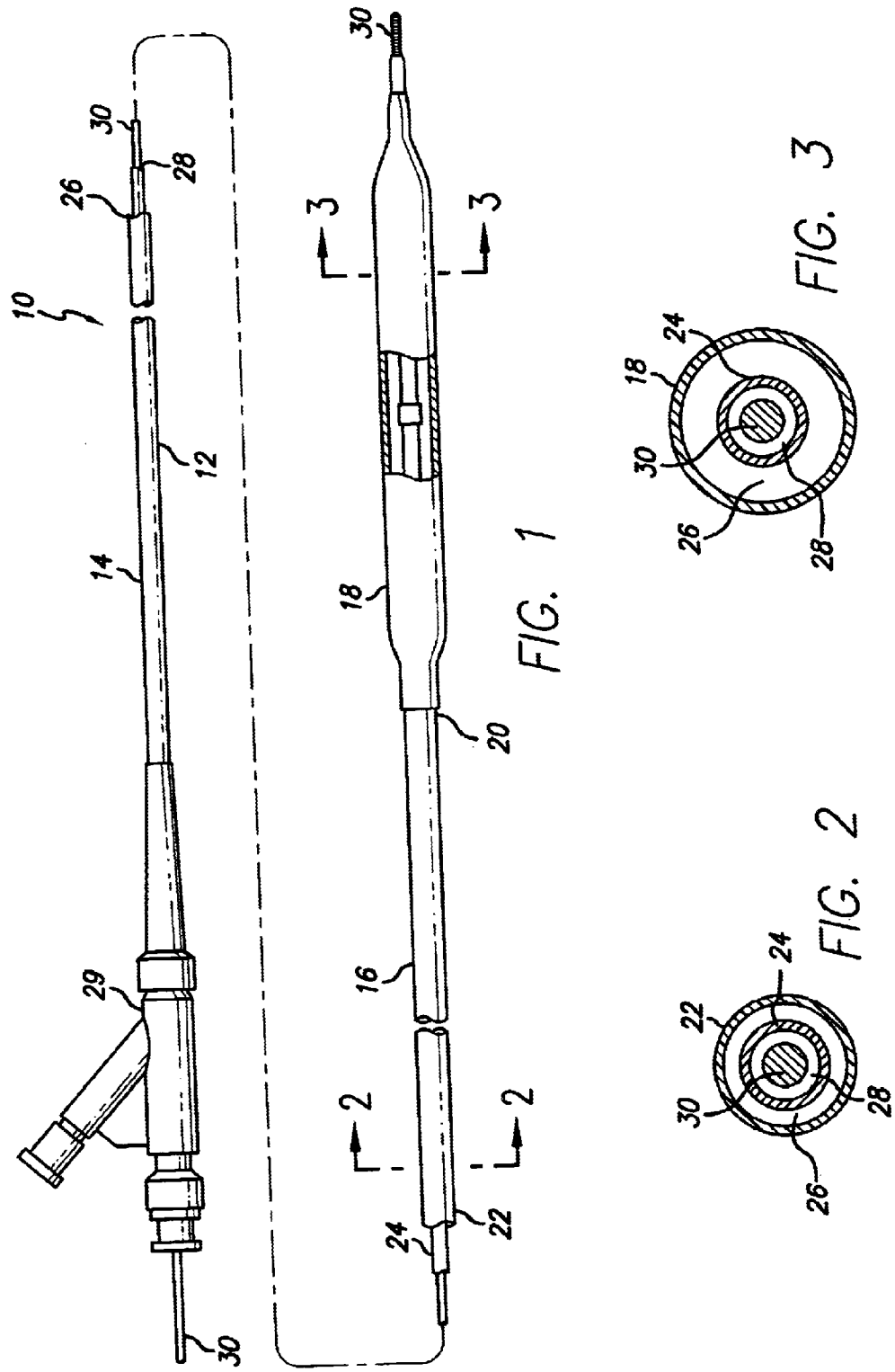

BALLOON BLOWING PROCESS WITH METERED VOLUMETRIC INFLATION

BACKGROUND OF THE INVENTION

This invention generally relates to intravascular balloon catheters, such as are used in percutaneous transluminal coronary angioplasty (PTCA) and stent delivery.

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and thereby increase the blood flow there through. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced until the preshaped distal tip of the guiding catheter is disposed within the aorta adjacent the ostium of the desired coronary artery, and the distal tip of the guiding catheter is then maneuvered into the ostium. A balloon dilatation catheter may then be advanced through the guiding catheter into the patient's coronary artery over a guidewire until the balloon on the catheter is disposed within the stenotic region of the patient's artery.

The balloon is inflated to open up the arterial passageway and increase the blood flow through the artery. Generally, the inflated diameter of the balloon is approximately the same diameter as the native diameter of the body lumen being dilated so as to complete the dilatation but not over expand the artery wall. After the balloon is finally deflated, blood flow resumes through the dilated artery and the dilatation catheter can be removed therefrom.

In a large number of angioplasty procedures, there may be a restenosis, i.e. reformation of the arterial plaque. To reduce the restenosis rate and to strengthen the dilated area, physicians now frequently implant an intravascular prosthesis called a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent is left in place within the artery at the site of the dilated lesion.

Catheter balloons are typically manufactured independently of the catheter and then secured to the catheter with an adhesive or other bonding method. In standard balloon manufacture, an extruded polymer tube is blown biaxially under the action of axial tension, internal pressure and heat into a mold. The polymeric tube has an initial outer diameter, and is elongated axially until the polymeric tube exhibits resistance to further stretching. This is generally achieved at about 2 to 4 times the original length, the outer diameter is roughly 40% to 50% of the original outer diameter, and the wall thickness is about 50% of the original wall thickness. The blowing temperature is generally above the glass transition temperature of the polymer, but below its melting point. The pressurization fluids may include air, nitrogen or argon. Additionally, pressurized liquids such as water or alcohol have been used. The polymer tube may either be simultaneously stretched in the radial and axial directions, or sequentially, by first stretching axially and then radially.

The balloon blow-up-ratio (BUR) is defined as the ratio of the outer diameter of the blown balloon to the inner diameter of the extruded tubing. For a given balloon wall thickness, the rupture strength generally increases and the radial compliance decreases as the balloon BUR increases. This is due to the increase in the molecular orientation of the polymer with increased stretching. For standard pressure driven blow molding, typical BURs range from about 4.5 to about 7.0 depending on the material and the product application. Beyond a critical BUR for a given polymer, the balloon blowing process becomes unstable and the tubing often ruptures before a balloon is formed. For some materials, defects such as microtears appear above a certain BUR because of the combination of the high rate and high extent of material stretching.

In the standard pressurized blow molding process, an initiated bubble rapidly grows in diameter until it is constrained by the mold wall. The hoop stress in the wall of the tubing, as it grows into a balloon may be approximated by the expression:

$$\sigma_h = \frac{P \cdot R}{\delta}$$

where P is the inflation pressure, R is the mean radius of the polymeric tube at any time during the inflation and δ is the wall thickness of the tubing. For a balloon to be initiated from the tubing, the inflation pressure should be such that the wall hoop stress exceeds the material resistance (typically the yield stress) to stretching at the blowing temperature. Once a balloon is initiated from the tubing, it grows rapidly in size until it touches the mold wall. As the balloon grows, the radius increases and the balloon wall thickness decreases. This results in a rapid increase in the wall hoop stress during constant pressure blowing. If the wall hoop stress of the growing balloon exceeds the ultimate hoop strength of the material, rupture will occur. The situation is exacerbated for high BURs. It would be desirable to reduce the blowing pressure as the balloon grows, but it is difficult to modulate pressure in the rapid time scale of tubing growth into a balloon. What has been needed is a method of blowing balloons that will allow greater control of the process.

SUMMARY OF THE INVENTION

The present invention is directed to a method of forming a balloon for a catheter. The method generally includes providing a polymeric tubular member having an inner lumen and a longitudinal axis, sealing off one end of the tubular member, introducing an incompressible fluid into the lumen at a volumetric flow rate, and expanding the polymeric tubular member to a desired outer diameter. The invention is also directed to a balloon formed by the method of the invention in which the polymeric tubular member is expanded to form the balloon by volumetric metering of an incompressible fluid into the lumen of the polymeric tubular member. In a presently preferred embodiment, the balloon is formed of a co-polyester such as Hytrel available from E.I. DuPont de Nemours, or Arnitel available from DSM Engineering, and in one embodiment, a polyester block copolymer having a polybutylene terephthalate hard segment. In a presently preferred embodiment, the balloon blow up ratio is about 5 to about 8. In one embodiment, the balloon blow up ratio is at least about 6.

The polymeric tubular member is typically radially expanded at elevated temperature. The temperature of the tubular member during expansion is generally higher than the glass transition temperature of the polymer, but lower than the melting point. In one embodiment, axial tension is applied to the polymeric tubular member to lengthen the polymeric tubular member during formation of the balloon. The axial tension may be applied before the infusion of the incompressible fluid.

Introduction of an incompressible fluid into the tubular member will cause an increase in the lumen volume by an amount equal to the amount of fluid infused into the lumen. The rate of fluid infusion may be slowed once a balloon is initiated upon material yielding, in order to stabilize the growing balloon. Because of the volumetric control of the infusion, the initiated radially expanding section, or bubble, or the balloon does not grow in volume beyond the volume of fluid infused. This control of bubble growth rate reduces the possibility of abrupt rupturing of the bubble as it increases in diameter, and therefore allows the tubular member to be blown to a higher BUR. As a consequence of the increased BUR, the process of this invention will lead to balloons with thinner walls and hence lower profile balloon catheters, as compared to balloons of the same hoop strength or radial compliance made with today's methods. A balloon made according to the method of the invention will have a higher hoop strength and lower radial compliance as compared to a balloon having the same wall thickness but made from conventional techniques in which internal pressure is delivered to the polymeric tubular member through a compressible fluid such as air or nitrogen. The method of the invention allows for high BURs without causing balloon defects such as microtears.

Additionally, a thin walled balloon of high hoop strength and low compliance is needed in the art. These and other advantages of the invention will become more apparent from the following detailed description and exemplary drawings.

BRIEF DESCRIPTION OF THE DRAWINGS

FIG. 1 is an elevational view, partially in section, of a balloon catheter embodying features of the invention including a balloon manufactured by a method which embodies features of the invention.

FIG. 2 is a transverse cross sectional view of the catheter of FIG. 1 along line 2—2.

FIG. 3 is a transverse cross sectional view of the catheter of FIG. 1 along line 3—3.

DETAILED DESCRIPTION OF THE INVENTION

Figure 4:
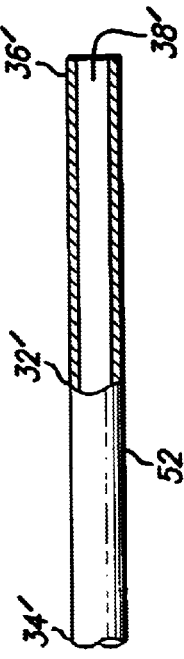
FIG. 4 is an elevational view, partially in section, of a polymeric tubular member useful in making a balloon according to a method of the invention, having an inner lumen and a longitudinal axis.

A catheter 10 embodying features of the invention has an elongated shaft 12 with a proximal end 14 and a distal end 16, and at least one lumen therein. A balloon 18 is disposed about a distal portion 20 of the distal end 16 of the catheter 10. The catheter shaft 12 has an outer tubular member 22 and an inner tubular member 24 disposed within the outer tubular member 22 and defining, with the outer tubular member 22, an annular inflation lumen 26. Inflation lumen 26 is in fluid communication with the inflatable balloon 18. Inflation fluid introduced into an inflation port on an adapter 29 located at the proximal end 14 of the catheter shaft 12, travels through the inflation lumen 26, and inflates the balloon 18. The inner tubular member 24 has an inner lumen 28 extending therein, which is configured to slidably receive a guidewire 30 suitable for advancement through a patient's coronary arteries. The distal extremity of the balloon 18 is sealingly secured to the distal extremity of the inner tubular member 24, and the proximal extremity of the balloon 18 is sealingly secured to the distal extremity of the outer tubular member 22.

FIGS. 4–7 illustrate the manufacture of balloon 18 according to a method which embodies features of the invention. A polymeric tubular member 32 is provided. The polymeric tubular member 32 has a proximal end 34, a distal end 36 and a lumen therein 38. The polymeric tubular member 32 may be formed of any material having suitable characteristics for an intravascular balloon. Such polymers include polyolefins and polyolefin copolymers, polyamides and polyamide block copolymers, polyethylene terephthalate and polyester block copolymers, and thermoplastic polyurethane block copolymers. The process of this invention is particularly useful for producing high hoop strength polyester block copolymer balloons having a polybutylene terephthalate hard segment. The polybutylene hard segmented of these copolymers crystallizes at a very rapid rate when cooled from the melt state, making it difficult to reduce the crystallinity of the extruded tubular member. The relatively high crystallinity of the polymeric tubular member 32 offers high resistance to stretching and limits the BUR of balloons produced by standard methods to about 5.0. The method of the invention provides catheter balloons having BURs of 6.0 or greater, resulting in a high hoop strength balloon. Examples of such copolymers include Hytrel® polymers from E.I. DuPont de Nemours, Arnitel® polymers from DSM Engineering, and Pelprene® polymers from Toyobo Co.

Ltd. The soft segment of the copolymer is typically a polyether, although other soft segments may be used, such as polyesters.

In one embodiment, the polymeric tubular member 32 is axially stretched. The polymeric tubular member 32 may be stretched about 1.5 to about 6 times the original length, preferably about 1.5 to about 4 the original length. This may be accomplished by methods known in the art such as stretching under axial tension, or necking with a die. Heat may optionally be applied to raise the temperature of the tubing above the glass transition temperature of the polymer, but below the melting point during axial stretching.

Figure 5:
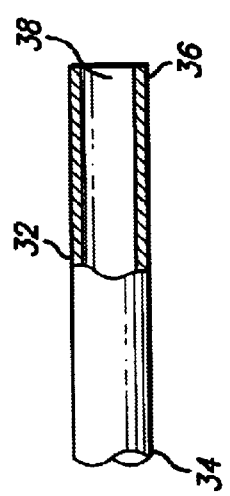
FIG. 5 is an elevational view, partially in section, of the polymeric tubular member of FIG. 4 after being axially stretched.

FIG. 5 illustrates the polymeric tubular member 32 after being axially stretched. The axially stretched polymeric tubular member 32' has a greater length and smaller inner diameter and wall thickness after being axially stretched. Before the stretch, the inner diameter of the tubular member 32 is about 12.5 percent to about 20 percent of the balloon outer diameter, and the wall thickness of the tubular member 32 is about 7 to 13 times the wall thickness of the balloon outer diameter. After the stretch, the inner diameter of the tubular member 32' is about 40 percent to 95 percent of the inner diameter of the nonstretched tubular member 32, and the wall thickness of the tubular member 32' is about 40 percent to 95 percent of the wall thickness of the unstretched tubular member 32.

Figure 6:
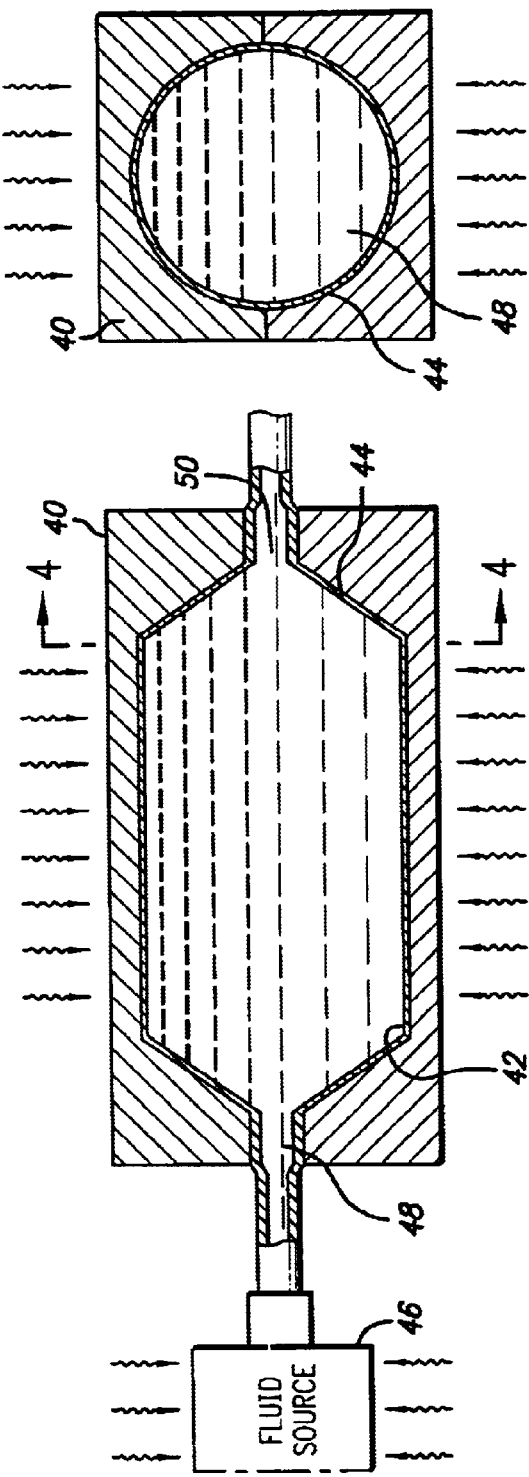
FIG. 6 is a longitudinal cross sectional view of the polymeric tubular member of FIG. 5 after placement into a balloon mold and introduction of incompressible fluid according to a method of the invention.
Figure 7:
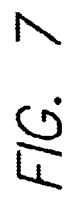
FIG. 7 is a transverse cross sectional view of the system of FIG. 6 along line 4—4.

The polymeric tubular member 32' is then placed into a mold 40 (FIG. 6). The mold 40 is about 5 mm to about 40 mm long, with an inner diameter of about 1.5 mm to about 10 mm. In some embodiments, the axial stretch described in relation to FIG. 5 is performed with the polymeric tubular member 32 within the mold 40. Additionally, the invention may be utilized without a mold if no specific final shape is required. In the embodiment described in FIGS. 4–7, the polymeric tubular member 32 was axially stretched prior to placement in the mold 40 and the stretched polymeric tubular member 32' was radially expanded in mold 40. The mold 40 has an inner wall 42, which defines an inner diameter. The mold 40 inner diameter is equal to the desired outer diameter of a balloon 44.

The lumen 38 is in fluid communication with a fluid source 46. The fluid source 46 such as a syringe pump is capable of delivering an incompressible fluid 48 into the balloon with a programmable flow rate and infusion volume. Heat may be applied to the fluid 48 prior to its introduction into the lumen 38 of the polymeric tubular member 32'. Heat may also be applied to the mold 40 during introduction of the fluid 48.

However, the invention does not require any heat added to the fluid 48 or to the mold 40. The proximal end 34' of the polymeric tubular member 32' is in fluid communication with the fluid source 46, as is the lumen 38'. The distal end 36' of the polymeric tubular member 32' is sealed against fluid flow. The seal (not shown) may be a reversible seal, or the distal end 36' may be cut after the balloon 44 is formed to recreate a lumen 50 through the balloon 44. The fluid 48 is then introduced into the lumen 38' of the polymeric tube 32', causing radial expansion. The fluid 48 is preferably water, although water glycerol mixtures are preferred when balloon blowing temperatures in excess of about 90 degrees C. The fluid 48 should be non-reactive with the material which forms the polymeric tubular member 32', and does not plasticize the balloon material. Additionally, the fluid 48 should be a liquid at the temperature of the blowing, typically about 70 degrees C to about 110 degrees C.

The fluid 48 is introduced into the polymeric tubular member lumen with a controlled volumetric flow rate. The volumetric flow rate is controllable, and therefore reduces the likelihood of rupture during the expansion of the tubular member 32'. Typically, the incompressible fluid 48 is introduced at a predetermined metered volumetric flow rate of about 0.1 cubic millimeters per second to about 100 cubic millimeters per second, preferably about 0.5 to about 30 cubic millimeters per second. The infusion of fluid 48 into the mold 40 is stopped after the balloon 44 is blown to the desired outer diameter, and the outer wall 52 meets the inner wall 42 of the mold 40. The contact of the balloon wall 52 with mold inner wall 42 may be observed by monitoring the pressure of the fluid. Contact will be signaled through the rapid buildup in fluid pressure. The fluid pressure may be maintained for a period of time, with the balloon at elevated temperature to heat-set the balloon for improved mechanical properties and dimensional stability.

The fluid source 46 is then disengaged, and the fluid 48 inside the balloon 44 is removed. The process may also include cleaning the inside of the balloon 44 to remove any liquid remnants. Such cleaning processes may include a flush with additional liquid, a flush with a gaseous fluid to remove any liquid remnants, or the entire balloon in the mold may be heated to evaporate any liquid remnants.

The balloon 44 may also benefit from cooling under pressure (not shown) to set the polymer chain orientation while in the mold 40. Some polymers may require a rapid cooling to maintain the polymer chain orientation. One option for the cooling process would be to flush the balloon 44 with a cooler liquid while maintaining the shape of the balloon 44. Another possibility would be a flush with a cool gaseous fluid. The gas may be pressurized to maintain the shape of the balloon. The cooling and cleaning steps could be combined, for example, by flushing with a cooling liquid or gas which also cleans any liquid remnants. After any cleaning or cooling process, if one is required, the balloon 44 is removed from the mold and placed on the distal portion 20 of the distal end 16 of the catheter shaft 12 and secured thereto.

The balloon of this invention will have a wall thickness, single wall basis of not u greater than about 0.002 inches and a wall hoop strength of greater than about 15,000 psi to about 22,000 psi. The radial growth of the balloon diameter from the rated nominal pressure to the rated burst pressure will be not greater than about 20% of the nominal diameter, preferably no greater than about 10% of the nominal diameter.

The catheter 10 illustrated in FIG. 1 is an over-the-wire dilatation catheter.

However, one of skill in the art will readily recognize that the balloons of this invention may also be used with other types of intravascular catheters, such as stent delivery balloon catheters, and rapid exchange balloon catheters. Rapid exchange catheters have a distal guidewire port and a proximal guidewire port spaced a short distance from the distal end of the catheter and a substantially greater distance from the proximal end of the catheter, and a short guidewire lumen extending between the proximal and distal guidewire ports in a distal section of the catheter.

Although the invention has been described in terms of preferred embodiments, certain modifications may be made without departing from the scope of the invention. Moreover, although individual features of embodiments of the invention may be shown in some of the drawings and not in others, those skilled in the art will recognize that individual features of one embodiment of the invention can be combined with any or all the features of another embodiment.

What is claimed is:

1. A method of forming a balloon for a catheter, comprising:
   (a) providing a polymeric tubular member having an inner lumen and a longitudinal axis;
   (b) introducing an incompressible fluid into the inner lumen at a volumetric flow rate; and
   (c) expanding the polymeric tubular member to a desired outer diameter by controlling the volume of introduced incompressible fluid.

2. The method of claim 1 wherein the volumetric flow rate is about 0.5 to about 30 cubic millimeters per second.

3. The method of claim 1 further comprising, after (a), placing the polymeric tubular member in a mold having an inner diameter equal to the desired outer diameter of the expanded polymeric tubular member.

4. The method of claim 3 wherein the polymeric tubular member has an inner diameter, and the mold inner diameter is about 5 to about 8 times greater than the inner diameter of the polymeric tubular member, and the polymeric tubular member is expanded into contact with an inner surface of the mold.

5. The method of claim 3 wherein the polymeric tubular member has an inner diameter, and the mold inner diameter is at least about six times greater than the inner diameter of the polymeric tubular member and the polymeric tubular member is expanded into contact with an inner surface of the mold.

6. The method of claim 3 including heating the mold prior to placing the polymeric tubular member within the mold, so that the polymeric tubular member is heated in the mold.

7. The method of claim 6, wherein the mold is heated to a temperature of about 60° C. to about 120° C.

8. The method of claim 3 including heating the mold after placement of the polymeric tubular member within the mold, so that the polymeric tubular member is heated in the mold.

9. The method of claim 8, wherein the mold is heated to a temperature of about 60° C. to about 120°C.

10. The method of claim 1 further comprising applying force on the polymeric tubular member proximal and distal ends to lengthen the polymeric tube along the polymeric tube longitudinal axis.

11. The method of claim 6 wherein the polymeric tubular member has an original wall thickness, and after lengthening, the polymeric tubular member has a wall thickness of about 40% to about 95% of the polymeric tubular member original wall thickness.

12. The method of claim 1 including, prior to (b), heating the incompressible fluid, so that the polymeric tubular member is heated by the incompressible fluid.

13. The method of claim 12 wherein the incompressible fluid is heated to a temperature of about 60° C. to about 120° C.

14. The method of claim 1 wherein the polymeric tubular member is softened prior to placement of the polymeric tubular member within the mold.

15. The method of claim 1 wherein the polymeric tubular member comprises a polyester copolymer and has an inner diameter and an outer diameter before being expanded, and the polymeric tubular member is expanded the desired outer diameter which is at least about six times greater than the polymeric tubular member inner diameter.

16. A method of forming a balloon for a catheter, comprising
 (a) providing a balloon mold;
 (b) placing within the mold a polymeric tubular member comprising a polyester copolymer having an outer diameter and an inner diameter; and
 (c) expanding the polymeric tubular member in a single step to a final outer diameter of at least about six times greater than the polymeric tubular member inner diameter.

17. A catheter balloon having a wall thickness, single wall basis, of less than about 0.002 inches and a wall hoop strength of greater than about 15,000 psi to about 22,000 psi, wherein the balloon is formed of a material selected from the group consisting of a copolymer of polybutylene terephthalate hard segment and polyester soft segment, and a copolymer of polybutylene terephthalate hard segment and polyether soft segment.

18. A catheter balloon made by a process comprising:
 a) providing a polymeric tubular member having an inner lumen;
 b) introducing incompressible fluid into the inner lumen at a predetermined volumetric flow rate; and
 c) expanding the polymeric tubular member to a desired outer diameter by controlling the volume of introduced incompressible fluid.

19. The catheter balloon of claim 18, wherein the balloon comprises a polyester copolymer.

* * * * *

UNITED STATES PATENT AND TRADEMARK OFFICE
CERTIFICATE OF CORRECTION

PATENT NO. : 6,620,128 B1
DATED : September 16, 2003
INVENTOR(S) : Murthy V. Simhambhatla It is certified that error appears in the above-identified patent and that said Letters Patent is hereby corrected as shown below:

<u>Column 4,</u>
Lines 42 and 43, move to continuation of line 41.

<u>Column 7,</u>
Line 20, change "6", to read -- 10 --.

Signed and Sealed this

Twenty-seventh Day of January, 2004

JON W. DUDAS
*Acting Director of the United States Patent and Trademark Office*